United States Patent [19]

Pez

[11] 4,231,948

[45] Nov. 4, 1980

[54] LITHIUM DICYCLOPENTADIENYL TITANIUM HYDRIDE COMPOSITIONS

[75] Inventor: Guido P. Pez, Boonton, N.J.

[73] Assignee: Allied Chemical Corporation, Morris Township, Morris County, N.J.

[21] Appl. No.: 957,392

[22] Filed: Nov. 3, 1978

[51] Int. Cl.$^3$ ................................................ C07F 7/28
[52] U.S. Cl. ............................................... 260/429.5
[58] Field of Search ...................................... 260/429.5

[56] References Cited

U.S. PATENT DOCUMENTS

| | | | |
|---|---|---|---|
| Re. 29,368 | 8/1977 | Pez | 260/429.5 |
| 3,306,919 | 2/1967 | Brantley et al. | 260/429.5 |
| 3,322,803 | 5/1967 | Vohwinkel et al. | 260/429.5 |
| 3,644,447 | 2/1972 | Joshi | 260/429.5 X |
| 3,776,932 | 12/1973 | Pez | 260/429.5 X |
| 3,980,684 | 9/1976 | Dines | 260/429.5 X |
| 4,024,169 | 5/1977 | Pez | 260/429.5 |

OTHER PUBLICATIONS

Pez. J.A.C.S. 98 8072-8078 (1976).

Primary Examiner—Helen M. S. Sneed
Attorney, Agent, or Firm—Robert A. Harman

[57] ABSTRACT

Novel lithium dicyclopentadienyl titanium hydride type compositions are described, useful as catalysts in converting ethylene to 1-butene, which is used in producing "polymer gasoline" for increasing the octane number of automotive gasolines. Methods for synthesizing the novel compositions are also described.

7 Claims, 2 Drawing Figures

LITHIUM DICYCLOPENTADIENYL TITANIUM HYDRIDE COMPOSITIONS

BACKGROUND OF THE INVENTION

1. Field of the Invention

This invention relates to novel lithium dicyclopentadienyl titanium hydride compositions, useful as catalysts in the conversion of ethylene to 1-butene, and processes for their synthesis.

2. Brief Description of the Background of the Invention Including Prior Art

As a result of the decreasing amounts of energy reserves in the world, particularly petroleum feedstocks, coupled with sharply rising increases in energy demands in the heavily industrialized regions of the world, intense research efforts are being conducted in developing new processes and new catalysts for synthesizing energy-yielding materials.

One aspect of this research is directed to increasing the octane number of automotive gasoline in order to increase the efficiency of fuel utilization in the internal combustion engine. "Polymer gas", a mixture produced by polymerizing 1-butene, 2-butene and ethylene, or mixtures thereof, can be added to automotive gasoline in order to increase the octane number, and thus, the efficiency of fuel utilization.

The starting component, 1-butene, can be produced industrially, in heterogeneous processes by the catalytic dehydrogenation of n-butane over chromic oxide on alumina catalyst at elevated temperatures, or by thermal and catalytic cracking of petroleum and natural gas fractions. See "Encyclopedia of Chemical Technology", by Kirk-Othmer, Second Edition, Volume 3, pp. 833-834, Interscience Publishers (1964).

Methods are also known for producing 1-butene from the catalytic dimerization of ethylene in solutions of Ziegler-type catalysts as described in German Pat. No. 1,034,169 (1958), Chem. Abstr. 54, 2087a; and German Pat. No. 1,039,055 (1958), Chem. Abstr. 54, 25992h.

New catalysts, which are inexpensively and easily prepared and which can homogeneously catalyze the dimerization of ethylene to 1-butene are desired in order to overcome the known disadvantages of the use of heterogeneous catalysts. Such disadvantages include surface poisoning effects, criticality of particle size, activation procedures and the like.

Novel cyclopentadienyl titanium complexes and nitrogen product complexes are described in the references: U.S. Pat. No. 3,776,932 (1973), U.S. Pat. No. Re. 29,368 (1977), U.S. Pat. No. 4,024,169 (1977), and J. Amer. Chem. Soc., 98, 8072-8078 (1976), by Guido Pez (said patents being assigned to Allied Chemical Corp.), hereby incorporated by reference, as being capable of converting ethylene to mixtures of ethane, butane, 1-butene and 1,3-butadiene. However, no specific mention of cyclopentadienyl titanium lithium hydride type complexes is made in the above references.

SUMMARY OF THE INVENTION

We have unexpectedly found a new class of compositions, namely, lithium dicyclopentadienyl titanium hydrides, which can be conveniently prepared and are very effective as catalysts in converting ethylene to 1-butene.

In accordance with this invention, there is provided a composition of the formula: LiRR'TiH, wherein R and R' are cyclopentadienyl rings of the empirical formula, $C_5H_5$, wherein the ring hydrogens may be independently substituted with one or more groups inert toward lithium metal, said rings being bonded to titanium by sigma-bonds, pi-bonds or mixtures thereof, and said composition exhibiting a $^{13}C$ nuclear magnetic resonance spectrum in deuterated benzene, in which observed values for the chemicals shifts of the ring carbons in R are different from the observed values for ring carbons in R', and said composition exhibiting an infrared spectrum in deuterated n-hexadecane in which a titanium metal-hydride absorption band is observed in the region of about 1250-1450 cm$^{-1}$.

Also provided is a process for producing the subject compositions comprising contacting metallic lithium with a dititanium complex of the formula:

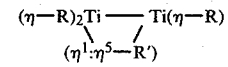

wherein the ($\eta$—R) radicals are cyclopentadienyl rings, bonded to titanium through five carbon atoms, and independently having the formula, $C_5H_5$, wherein the ring hydrogens may be independently substituted with one or more groups inert toward lithium metal, and wherein the ($\eta^1$:$\eta^5$—R') radical is a cyclopentadienyl ring, bonded to titanium by a mixture of $\eta^1$ and $\eta^5$ bonds, and having the empirical formula, $C_5H_4$, wherein the ring hydrogens may be independently substituted with one or more groups inert toward lithium metal; in an inert solvent therefor, at a temperature of about $-10°$ to $+60°$ C. in the absence of elemental oxygen and water, and initial molar ratio of metallic lithium to said dititanium complex of about 10:1 to 1:1, in the presence of a polynuclear aromatic hydrocarbon solubilizing agent for lithium, soluble in said solvent.

Further provided is a process for producing the subject compositions comprising contacting metallic lithium with a titanium compound of the formula: $R_2TiX_a$, or dimers thereof, wherein independently the radicals R are cyclopentadienyl rings, each having an empirical formula, $C_5H_5$, and wherein the ring hydrogens may be independently substituted with one or more groups inert toward lithium metal, X being halogen, and the subscript a being one or two; in diethyl ether, and in the presence of a polynuclear aromatic hydrocarbon solubilizing agent for lithium, soluble in diethyl ether, at a temperature of about $-80°$ to $+80°$ C., in the absence of elemental oxygen and water, and initial molar ratio of metallic lithium to said titanium compound of about 10:1 to 3:1.

Also provided is in a process for producing 1-butene including contacting gaseous ethylene with a solution of dimerization catalyst, in an inert solvent therefor, under pressure of about 1 to 100 atmospheres, at a temperature of about 0° to 100° C.; the improvement which comprises providing the subject composition described hereinabove as said catalyst.

DESCRIPTION OF THE INVENTION ARE PREFERRED EMBODIMENTS

The novel lithium titanium hydride compositions of this invention are actually lithium salts soluble in conventional organic solvents which are commonly used in catalytic reactions and processes. The structure of the subject compositions in terms of bonding characteristics and spatial geometry is not yet accurately known since a sufficiently well-ordered single crystal is not yet available. However, by analogy to the structure of various "titanocene" type compounds, described in *J. Amer. Chem. Soc.*, 98, 8072-8078 (1976), and from known bonding characteristics of other titanium complexes in the art it is strongly believed that each of the two cyclopentadienyl rings must be bonded to the titanium metal by either sigma bonds, pi bonds or mixtures thereof. By the term "pi-bond" designated in this case as $\eta^5$ using IUPAC nomenclature, (International Union of Pure and Applied Chemistry) as used herein, is meant a covalent bond formed between a titanium atom and the cyclopentadienyl ring by electrons, donated by the respective titanium and five carbon atoms, moving in orbitals extending above and below the plane of the cyclopentadienyl ring. By the term "sigma-bond" designated in this case as $\eta^1$ using IUPAC nomenclature as used herein, is meant a covalent bond formed between a titanium atom and one carbon atom of a cyclopentadienyl ring by electrons, donated by the respective atoms, and directed along the line joining the centers of the two atoms. By the term "mixtures" thereof, as used herein, includes hybrid bonding between a titanium atom and 2, 3 or 4 carbon atoms of a cyclopentadienyl ring ligand, which is termed $\eta^2$, $\eta^3$, $\eta^4$ bonding, respectively, by accepted IUPAC nomenclature. The term "mixture thereof" also encompasses bonding which is distinctly a mixture of sigma and pi bonding and designated in this case as $\eta^1:\eta^5$ bonding using IUPAC nomenclature. Where the number of carbon atoms of the ligand attached to the metal atom is obvious from the stated formula, no superscript is used with the $\eta$ nomenclature, thus, for example, $Li(\eta-C_5H_5)(C_5H_5)TiH$ and $Li(\eta-C_5H_5)(C_5H_5)TiH$ are equivalent. The symbol "$\mu$" designates a bridging between a cyclopentadienyl ring and two titanium atoms (IUPAC).

Figure 1:
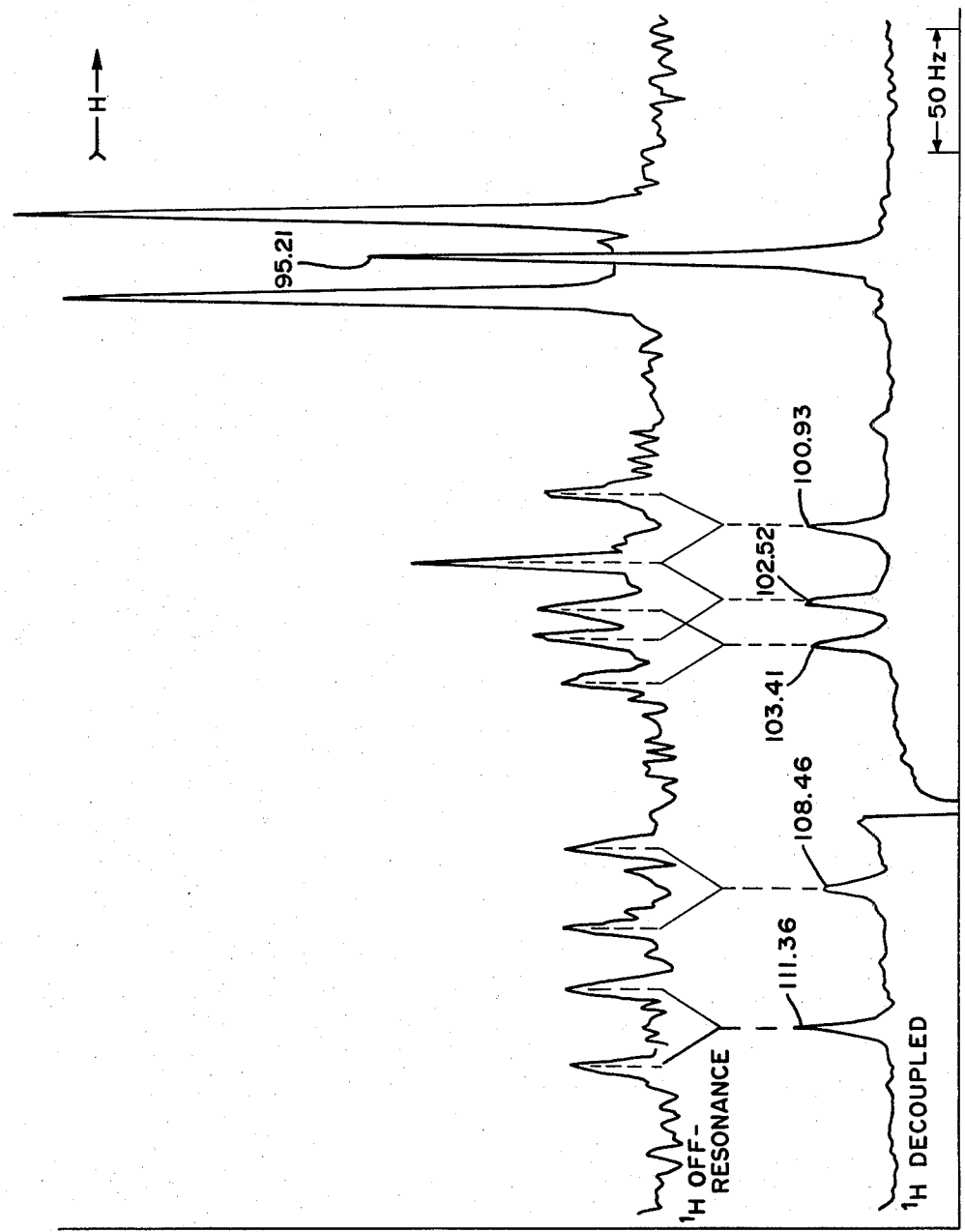
FIG. 1 is a $^{13}C$ nuclear magnetic resonance spectrum taken at 20 MHz, of Li($\eta$—$C_5H_5$)($C_5H_5$)Ti—H in deuterated benzene containing tetramethylethylenediamine. Chemical shifts are in ppm versus tetramethylsilane (calculated via $C_6D_6$).

The physical properties of the subject compositions, as determined spectroscopically, clearly indicate that the two cyclopentadienyl rings are not equivalent and that they are differently bonded to titanium. Evidence for this bonding difference is substantiated by the proton decoupled $^{13}C$ nuclear magnetic resonance (NMR) spectrum of the unsubstituted compound, $Li(\eta-C_5H_5)(C_5H_5)Ti-H$, in deuterated benzene, containing tetramethylethylenediamine to aid in solubilizing the compound, as illustrated in the lower curve of FIG. 1, wherein the observed values for the chemical shifts of the five ring carbons of one cyclopentadienyl ring, designated as ($\eta-C_5H_5$), are all equivalent and occur in one combined absorption peak at 95.21 ppm downfield vs. tetramethylsilane standard, TMS, taken as 0 ppm. The observed values for the chemical shifts of the ring carbons in the other cyclopentadienyl ring, designated as ($C_5H_5$), occur at five non-equivalent positions ranging from 100.93 to 111.36 ppm relative to TMS standard. The upper curve of FIG. 1, illustrates the off-resonance, protoncoupled, $^{13}C$ NMR spectrum which shows that there is one hydrogen atom per each carbon atom in each of the cyclopentadienyl rings ($C_5H_5$ and $\eta-C_5H_5$). This technique for determining the structural and bonding equivalency and nonequivalency of carbon atoms in organic molecules is well known and accepted in the art.

By the term "substituted", as used herein and applied to the cyclopentadienyl rings, is meant that the ring hydrogens may be independently substituted by one or more groups, not exceeding five groups per cyclopentadienyl ring, which are inert toward lithium metal, specifically under the conditions of solution in an inert organic solvent at room temperature. This requirement of inertness toward reaction with lithium metal stems from the fact that the subject compositions are generally prepared from the precursor cyclopentadienyl titanium compounds, described in the above references by Guido Pez, by reaction with lithium metal. Thus, the term does not embrace substituent groups which are replaceable by reaction with lithium, such as the halogens or groups containing active hydrogen, such as hydroxy. Representative examples of suitable substituents include $C_1-C_4$ linear or branched alkyl, $C_1-C_4$ linear or branched alkoxy, and phenyl. Where the cyclopentadienyl rings are substituted, preferred substituents are the above-described $C_1-C_4$ and alkyl, and particularly methyl. Where the cyclopentadienyl ring is substituted, it is preferably mono-substituted.

Figure 2:
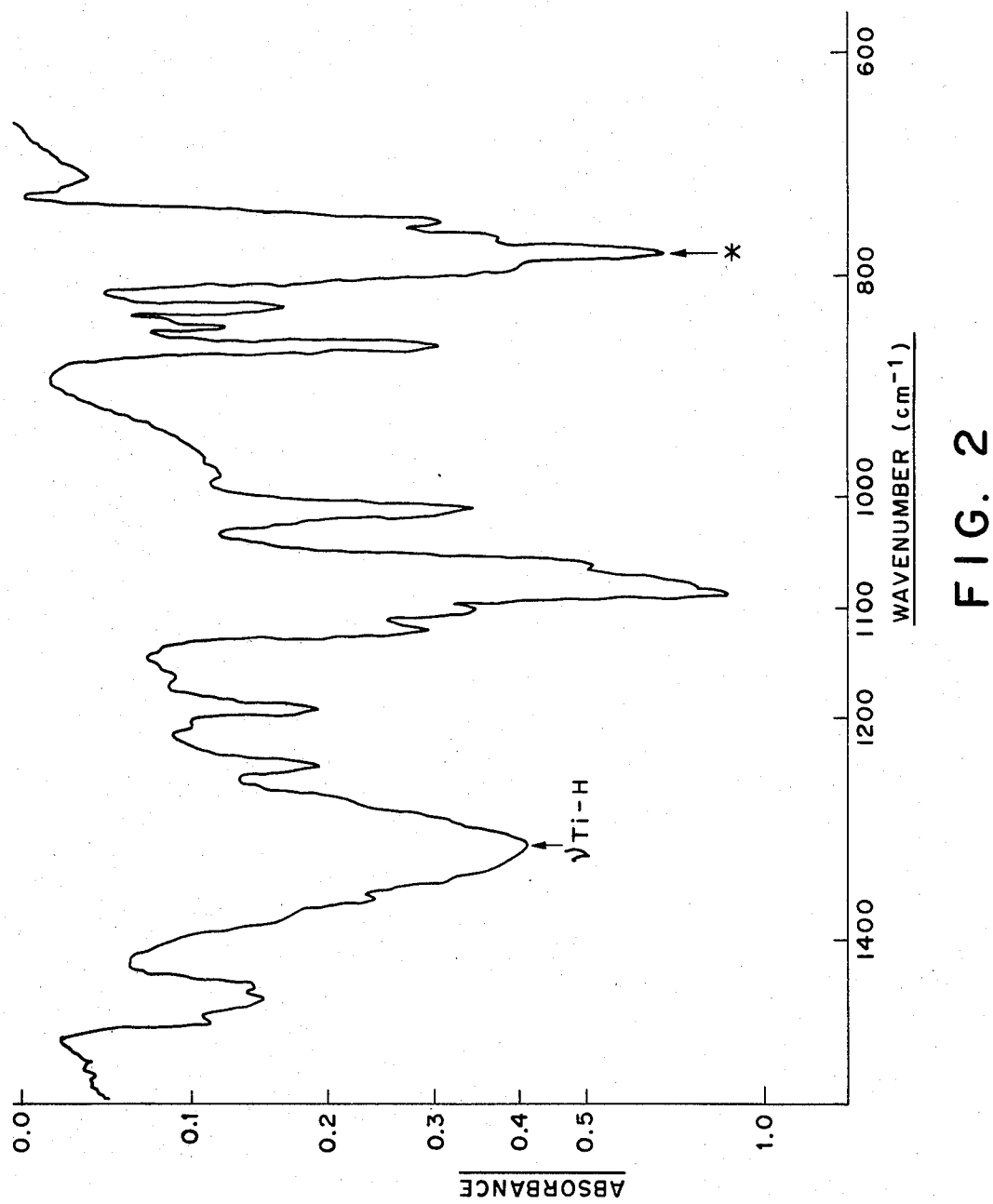
FIG. 2 is an infrared spectrum of crystalline Li(-$\eta$—$C_5H_5$)($C_5H_5$)Ti—H.($CH_3OCH_2CH_2OCH_3$) adduct

The hydride character of the subject composition resides in the titanium metal-hydride bond, i.e. Ti-H. By the term "hydride", as used herein, is meant that the hydrogen attached to the titanium metal atom in the subject composition can support a negative charge. Evidence for the metalhydride bond in the subject compositions is provided by the fact that they exhibit as infrared spectrum, in a mull of deuterated n-hexadecane, between two potassium bromide discs, which contains an absorption band at about 1250 to 1450 cm$^{-1}$, which is generally broad and intense. The exact position of the band within this range is largely dependent upon the nature of the solvent used to solvate the lithium cation in the resulting complex. Thus, for crude Li $(\eta-C_5H_5)(C_5H_5)Ti-H$, obtained from the first described process herein using diethyl ether as solvent, the Ti—H absorption band occurs at 1390 cm$^{-1}$; whereas in a crystalline form of the compound prepared in 1,2-dimethoxyethane as solvent, the Ti—H absorption band occurs at 1315 cm$^{-1}$, as illustrated in FIG. 2. Substituents on the cyclopentadienyl rings, as defined herein, will not significantly change the region of absorption of the metal-hydride band outside of this stated region.

Further evidence for the presence of the metalhydride bond in the subject compositions is furnished by reaction of the subject compositions with methyl iodide wherein it is found that approximately one mole of methane is liberated by reaction of at least one mole of methyl iodide with one mole of subject composition. This technique is well known and accepted in the art as evidence of the presence of a hydride moiety.

Since the subject compositions contain a lithium cation, the compositions are readily soluble in solvents which act as chelating agents for the lithium cation by virtue of the fact that the solvents contain atoms having unshared non-bonding electrons such as an oxygen and nitrogen. Representative examples include diethyl ether, 1,2-dimethoxyethane (DME), 1,2-diethoxyethane, p-dioxane, tetrahydrofuran, crown ethers such as 15-crown-5 (1,4,7,10,13-pentaoxycyclopentadecane), 18-crown-6 (1,4,7,10,13,16-hexaoxycyclooctadecane), dibenzo and dicyclohexyl derivatives thereof, diamines such as N,N,N',N'-tetramethylethylenediamine, and cryptates, being bicyclic bridgehead diamines, having oxymethylene bridges, and the like. It is to be understood that adducts formed between the subject compositions and organic compounds, possessing the ability to chelate lithium, are also encompassed as compositions within the scope of this invention. Adducts formed from other chelating agents, not specifically described herein, will also be equivalent and obvious to one skilled in the art.

Other physical properties of the compositions in addition to the observed $C^{13}$ nuclear magnetic resonance behavior and infrared spectrum include a reddish brown color of the solid compositions and a proton nuclear magnetic resonance spectrum which shows a metal-hydride resonance at $-4.64$ ppm, upfield from tetramethylsilane.

Representative examples of the invention compositions include $Li(CH_3—C_5H_4)(\eta—C_5H_5)Ti—H$, $Li(C_5H_5)(\eta—CH_3—C_5H_4)Ti—H$, $Li(\eta—CH_3—C_5H_4)(p—CH_3—C_5H_4)Ti—H$, and $Li([\eta—C_5(CH_3)][C_5(CH_3)_5]Ti—H$. Preferred composition is $Li(\eta—C_5H_5)(C_5H_5)Ti—H$, useful as a catalyst in converting ethylene to 1-butene.

Also a subject of this invention is a process for preparing the subject compositions in which lithium metal is contacted in a solution of inert solvent in the presence of a polynuclear aromatic hydrocarbon solubilizing agent for lithium, at a temperature of about $-10°$ to $+60°$ C. in the absence of elemental oxygen and water with a dititanium complex, in initial molar ratio of metallic lithium to dititanium complex of about 10:1 to 1:1, wherein the dititanium complex has the formula:

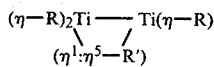

The ($\eta$—R) radicals in the above formula are cyclopentadienyl rings, bonded to Ti through five carbon atoms, and independently having the empirical formula, $C_5H_5$, and wherein the cyclopentadienyl ring hydrogen atoms may be independently substituted with one or more groups inert toward lithium, metal, said substituents being identical in nature to those described hereinabove for the subject compositions, and not exceeding five in number per cyclopentadienyl ring. The ($\eta^1:\eta^5$—R') radical is a cyclopentadienyl ring, bonded to titanium by a mixture of $\eta^5$ and $\eta^1$ bonds and having the empirical formula, $C_5H_4$, wherein the cyclopentadienyl ring hydrogens may be substituted with one or more groups inert toward lithium metal as described hereinabove, and not exceeding four in number.

An exact description of the nature of the bonding in these precursor cyclopentadienyl dititanium compounds is known in the art and described in *J. Amer. Chem. Soc.*, 98, 8072–8078 (1976), hereby incorporated by reference. Representative examples of cyclopentadienyl dititanium compounds useful in the process are the parent compound, $\mu—(\eta^1:\eta^5$-cyclopentadienyl)-tris($\eta$-cyclopentadienyl)dititanium (Ti-Ti), and substituted derivatives thereof, wherein the derivatives are formed by substituting the ring hydrogens on the respective cyclopentadienyl rings with said substituents as described hereinabove, for the subject compositions.

Preferred compound in the process is the above-described ring-unsubstituted parent compound.

The polynuclear aromatic hydrocarbon solubilizing agent for lithium, soluble in said solvent, is also essential for success of the reaction and includes naphthalene, anthracene, biphenyl and the like. A preferred agent is naphthalene. It is believed that the solubilizing agent reacts with lithium in the process to form a lithium cation-aromatic anion complex, a "metal arene", which thus aids the efficiency of the reaction process. The amount of solubilizing agent used is generally about 1 to 10 parts by weight per part of lithium metal and preferably about 1 to 2 parts by weight of lithium metal used.

The molar ratio of metallic lithium to said dititanium complex used is generally about 10:1 to 1:1 and preferably about 7:1.

The temperature of the process is generally conducted in the range of about $-10°$ to $+60°$ C. and preferably at about $20°$–$25°$ C.

Solvents useful in the process include those which have good solvating ability for the titanium compounds and include $C_2$-$C_6$ saturated aliphatic monoethers, $C_2$-$C_6$ linear saturated aliphatic diethers, $C_4$-$C_6$ cyclic saturated aliphatic monoethers, and $C_4$-$C_6$ cyclic saturated aliphatic diethers. Representative examples include diethyl ether, tetrahydrofuran, dioxane, 1,2-dimethoxyethane and the like. Preferred solvent is diethyl ether.

The amount of solvent used is generally about 100 to 500 parts by weight per part of titanium compound, although not limited thereto.

The process must be conducted in the absence of elemental oxygen and water to preclude decomposition of product composition and to prevent degradation or hydrolysis of the starting dititanium complex.

Various forms of apparatus may be used for the reaction and one which the inventor found useful was a hollow evacuable H-shaped glass apparatus having elongated vertical cylindrical sides connected by a horizontal tube of the same internal diameter as the vertical sides. An internal glass filter, positioned in the horizontal tube was used to filter the reaction product. Each bottom portion of the vertical sides of the H-tube, in an upright position, can serve as a reaction vessel in which the contents can be conveniently heated or cooled or stirred by the introduction of a magnetic stirring bar therein. The H-shaped apparatus can be used in a conventional dry box, which can be evacuated, or filled with argon, such that the entire reaction can be conducted under conditions in the absence of elemental oxygen and water.

Generally, dry lithium powder, a dititanium complex and inert solvent, such as diethyl ether, are placed into one of the vertical sides of the H-shaped apparatus, under a dry inert atmosphere, and the mixture is allowed to stir overnight at room temperature. The resulting mixture is then filtered by appropriately tipping the H-shaped apparatus such that the contents of the vertical tube are constrained to pass downward through the horizontal tube containing the glass filter frit. The obtained residue is extracted with solvent until no more soluble material remains. The solvent extracts and filtrate are combined and the solvent removed, in vacuo, resulting in a product composition of a purity in the range of about 60 to 80%. Purification can be accomplished in the apparatus by recrystallization from a suitable solvent such as diethyl ether or 1,2-dimethoxyethane.

Yields of the lithium titanium hydride composition are in the range of about 25% of theory based on starting dititanium complex.

In an alternative process of this invention for synthesizing the lithium titanium hydride compositions of this invention, metallic lithium is contacted with a titanium compound of the formula: $R_2TiX_a$, or dimers thereof, wherein independently the radicals R are cyclopentadienyl rings, each having an empirical formula, $C_5H_5$, and wherein the ring hydrogens may be substituted with one or more groups inert toward lithium metal, said groups being defined and described hereinabove, X being halogen, such as fluorine, chlorine, bromine or iodine, and a being one or two. The process is conducted in the presence of diethyl ether solvent for the titanium compound and in the presence of a polynuclear aromatic hydrocarbon solubilizing agent for lithium, said agent also being soluble in diethyl ether, in the absence of elemental oxygen and water, at a temperature of about −80° C. to +80° C., and at an initial molar ratio of metallic lithium to said titanium compound of about 10:1 to 3:1.

The titanium compounds useful in this alternative process include dicyclopentadienyl titanium monochloride and dichloride, dicyclopentadienyl titanium monobromide and dibromide, di-(3-methylcyclopentadienyl) titanium monochloride and dichloride, and the like. Preferred starting titanium compounds are the dichloride and dibromide of dicyclopentadienyl titanium.

Diethyl ether was the only solvent studied found to be effective in carrying out the invention process. Tetrahydrofuran and 1,2-dimethoxyethane were found to be to be inoperative. The amount of diethyl ether solvent used is generally about 100 to 500 parts by weight per part of said dititanium complex, although not limited thereto.

A polynuclear aromatic hydrocarbon solubilizing agent for the lithium metal is also used in this alternative process for the same reasons disclosed in the first-described process. Representative examples of such agents, and amounts used, are also specifically discussed hereinabove, in the initial process, and need not be reiterated. A preferred solubilizing agent is naphthalene, used in an amount of about 1 to 10 parts by weight per part of lithium metal, and preferably about 1 to 2 parts by weight of lithium metal used.

Temperature in this alternative process can be conducted in the range from about −80° C. to +80° C. A preferred process temperature is about 25° C.

The molar ratio of metallic lithium to said titanium compound is about 10:1 to 3:1 and preferably about 4:1.

Apparatus for conducting this alternative process can be of any conventional type designed to rigidly exclude elemental oxygen and water while performing the operations of heating, cooling, stirring and filtration. Apparatus which the inventor found useful is the H-shaped apparatus described hereinabove, for the first-described process.

In general, this alternative process comprises the previously described operations, in the first process, of adding the titanium compound and lithium powder into one vertical side of the H-shaped apparatus, under a dry inert atmosphere, and adding diethyl ether to the mixture and cooling the mixture with stirring to a temperature of about −80° C. The mixture is allowed to stir and warm to about −10° C. and a solvating agent for lithium such as naphthalene is then added. The contents are then allowed to stir and warm to room temperature and stirring is continued until the red-brown color persists. The resulting mixture is then filtered, in the H-shaped apparatus as previously described, the residue extracted with ether, and the ether filtrate and extracts are combined and then evaporated to yield the red-brown product. The product can be purified by recrystallization from 1,2-dimethoxyethane, diethyl ether or other like solvents, and preferably 1,2-dimethoxyethane.

Yields of product composition in this process are about 15 to 30% of theory based on starting titanium compound.

Advantage can be taken of the fact that the subject compositions are readily soluble in ethereal, aromatic, or alkylamine organic solvents, thus enabling the homogeneous catalytic dimerization of ethylene to 1-butene. It is believed that the reason the subject compositions are highly effective as homogeneous dimerization catalysts is due to the fact that a hydrogen atom is attached to the titanium metal in hydride form, and is thus very labile and available for hydride transfer with ethylene to initiate the dimerization reaction, via the formation of a transient anionic titanium (ethylene)ethyl intermediate. In addition, the spatial geometry of the solvated composition in solution, seems to promote the hydrogen transfer, and the removal of the 1-butene reaction product.

Accordingly, also a subject of this invention is an improved process for the homogeneous catalytic dimerization of ethylene to 1-butene. The elements of the process with respect to solvent, catalyst concentration, temperature, pressure, reaction time, yield, and apparatus are adequately described in the above-cited German Patents, and Chemical Abstract references thereto, and hereby incorporated by reference.

The improvement over the prior art process is the use of the subject compositions, disclosed herein, as homogeneous catalysts for the dimerization. A preferred catalyst for the dimerization is $Li(\eta-C_5H_5)(C_5H_5)Ti-H$, and a preferred solvent is N,N,N'N'-tetramethylethylenediamine.

The process includes contacting gaseous ethylene with a solution of the subject composition as dimerization catalyst, in an inert solvent therefor, under a pressure of about 1 to 100 atmospheres, at a temperature of about 0° to 100° C. Preferably, a solution of about 1 to 3 parts subject composition, as catalyst, in 100 parts by weight of solvent is used, preferably using N,N.N',N'-tetramethylethylene diamine as solvent, at about room temperature, under an initial atmosphere of gaseous ethylene at a pressure of about 10 atmospheres. The reaction contents, in a closed pressure vessel, are allowed to stir and contact until the absorption of ethylene by the solution becomes negligible. The product 1-butene is obtained in about a 90–99% conversion, based on reacted ethylene, and can be isolated and purified by conventional methods such as distillation.

Modifications and variations in the processes for producing the subject compositions and improved process for converting ethylene to 1-butene, utilizing the subject composition as catalysts, will be obvious to one skilled in the art from this disclosure.

The following examples are illustrative of the best mode of carrying out the invention as contemplated by us and should not be construed as being limitations of the scope and spirit of the instant invention.

EXAMPLE 1

Synthesis of Li($\eta$—C$_5$H$_5$)(C$_5$H$_5$)TiH from "Titanocene" and Lithium Metal Into an apparatus consisting of two 500 ml roundbottom flasks connected by a filter frit, was charged (into one flask) 0.4 grams of dry lithium powder (prepared from a lithium dispersion in oil), and 2.9 grams of $\mu$-($\eta^1$:$\eta^5$-cyclopentadienyl)-tris ($\eta$-cyclopentadienyl) dititanium (Ti-Ti) prepared by the procedure described in *J. Am. Chem. Soc.* 98, 8072 (1976), and 0.2 g. naphthalene, in the absence of air and moisture. To this solution was added 300 ml diethyl ether and the mixture was allowed to stir overnight at room temperature. The mixture was filtered and the residue further extracted with diethyl ether until a red-brown extract no longer remained. The ether extracts were combined with the filtrate and the ether solvents removed under reduced pressure. A red-brown residue was obtained (yield 0.9 grams). The product was insoluble in aromatic solvents, moderately soluble in ether and 1,2-dimethoxyethane and somewhat more soluble in tetrahydrofuran. An infrared spectrum of the product showed a broad intense band at 1390 cm$^{-1}$, characteristic of the titanium metal-hydride bond.

EXAMPLE 2

Synthesis of Li ($\eta$-C$_5$H$_5$) (C$_5$H$_5$)TiH from Titanocene Dichloride and Lithium Metal Into an apparatus consisting of two 1000 ml. round bottomed flasks, connected by a filter frit, was charged (into one flask) 30 gms. of dicyclopentadienyl titanium dichloride and 3.0 gms. of lithium powder in the absence of air and moisture. A side arm was connected to the same flask and charged with 2.5 gms. of naphthalene. Diethyl ester was distilled into the lithium/-dicylopentadienyl titanium dichloride mixture, and cooled to $-80°$ C. After the ether addition was completed, the mixture was stirred and when temperature reached about $-10°$ C., the naphthalene was added. The flask was cooled with ice water and then allowed to stir and warm spontaneously to room temperature. Stirring at about 23° C. was continued until the solution turned to a green, and then a red-brown color. The solution was filtered and the residue extracted with ether. The ether filtrate and extracts were combined and evaporated in vacuo and the resulting red-brown residue was washed with toluene. A red-brown powder was obtained in a yield of about 4.1 gms. Infrared and nuclear magnetic resonance spectra of the material proved to be identical to that described for the product in Example 1.

Purification and Characterization of Li($\eta$-C$_5$H$_5$) (C$_5$H$_5$)Ti-H (Preparation and handling of the above compound was carried out with rigid exclusion of air and moisture). The resulting crude red-brown product from Example 2 (400 mgs.) was loaded into an evacuable H-shaped glass apparatus having vertical sides separated by a horizontal glass tube of the same internal diameter containing a fritted tube. The apparatus allows filtration and recrystallization of air and moisture sensitive materials under reduced pressure. The product was dissolved in 1,2-dimethoxyethane (DME), 50 ml., in the bottom portion of one vertical side and the resulting solution was then concentrated to a volume of about 40 ml. The red-brown solution was filtered by tilting the apparatus such that the solution flowed from one vertical side through the glass filter to the other vertical side. The solvent was allowed to evaporate off slowly, at about 20° C., by cooling the other vertical side of the H tube to 15° C. A crystalline mass, covered by an oily layer, was seen after about 1 to 2 days of evaporation. The oily portion was washed with DME and the dry crystalline mass was redissolved. Crystallization resulted after evaporation over several days and afforded 160 mgs of black, brick-shaped crystals of Li($\eta$-C$_5$H$_5$)(C$_5$H$_5$)Ti-H(1,2-dimethoxyethane). Elemental analysis disclosed: Found: C, 61.05, H 7.42; Ti, 16.10; Li, 2.31; Expected: 60.89; H, 7.66; Ti, 17.34; Li, 2.51. A $^{13}$C nuclear magnetic resonance spectrum in deuterated tetrahydrofuran exhibited a single line at 94.91 ppm downfield (TMS=0 ppm) corresponding to 5 equivalent C$_5$H$_5$ carbon atoms plus a sequence of lines at 100.82, 102.0, 102.8, 109.1, 110.5 ppm, respectively, for 5 non-equivalent carbon atoms in the (C$_5$H$_5$) ring. This is basically the same $^{13}$C spectrum of the C$_5$H$_5$ rings as shown in FIG. 1 for the tetramethylethylenediamine adduct.

EXAMPLE 3

A glass reactor was charged with 200 mg. of Li($\eta$-C$_5$H$_5$)(C$_5$H$_5$) Ti-H, as prepared by the method of Example 2, and 15 ml N,N,N',N'-tetramethylethylene diamine. The reactor was charged with ethylene at 10 atm. pressure, and at room temperature. Upon continuing stirring, over a period of about 10 hours, the ethylene pressure decreased to a value of about 3 atmospheres. The product was analyzed by gas chromatography, and shown to be mainly 1-butene.

I claim:

1. A composition of matter of the formula: LiRR'TiH, wherein R and R' are cyclopentadienyl rings of the empirical formula, C$_5$H$_5$, wherein the ring hydrogens may be independently substituted with one or more groups inert toward lithium metal, said rings being bonded to titanium by sigma-bonds, pi-bonds or mixtures thereof, and said composition exhibiting a $^{13}$C nuclear magnetic resonance spectrum in deuterated benzene, in which observed values for the chemical shifts of the ring carbons in R are different from the observed values for ring carbons in R', and said composition exhibiting an infrared spectrum in deuterated n-hexadecane in which a titanium metal-hydride absorption band is observed in the region of about 1250-1450 cm$^{-1}$.

2. The composition of matter of claim 1 wherein R and R' are both unsubstituted cyclopentadienyl rings.

3. The composition of matter of claim 1 being an adduct formed with a chelating agent for lithium cation.

4. A process for producing the composition of matter of claim 1 comprising contacting metallic lithium with a dititanium complex of the formula:

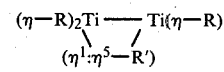

wherein ($\eta$—R) radicals are cyclopentadienyl rings, bonded to titanium through five carbon atoms, and independently having the empirical formula, C$_5$H$_5$, wherein the ring hydrogens may be independently substituted with one or more groups inert toward lithium metal, and wherein the ($\eta^1$:$\eta^5$—R') radical is a cyclopentadienyl ring, bonded to titanium by a mixture of $\eta^1$ and $\eta^5$ bonds, and having the empirical formula, $C_5H_4$, wherein the ring hydrogens may be independently substituted with one or more groups inert toward lithium metal; in an inert solvent therefor, at a temperature of about $-10°$ to $+60°$ C., in the absence of elemental oxygen and water, and initial molar ratio of metallic lithium to said dititanium complex of about 10:1 to 1:1, in the presence of a polynuclear aromatic hydrocarbon solubilizing agent for lithium, soluble in said solvent.

5. The process of claim 4 wherein the dititanium complex is $\mu$-($\eta^1$:$\eta^5$-cyclopentadienyl)-tris($\eta$-cyclopentadienyl)dititanium(Ti-Ti), the solvent is diethyl ether, the product is Li ($\eta$-$C_5H_5$)$C_5H_5$)TiH, and the polynuclear aromatic hydrocarbon is naphthalene.

6. A process for producing the composition of matter of claim 1 comprising contacting metallic lithium with a titanium compound of the formula: $R_2TiX_a$, or dimers thereof, wherein independently the radicals R are cyclopentadienyl rings, each having an empirical formula, $C_5H_5$, and wherein the ring hydrogens may be independently substituted with one or more groups inert toward lithium metal, X being halogen, and the subscript a being one or two; in diethyl ether solvent, and in the presence of a polynuclear aromatic hydrocarbon solubilizing agent for lithium, soluble in diethyl ether, at a temperature of about $-80°$ to $+80°$ C., in the absence of elemental oxygen and water, and initial molar ratio of metallic lithium to said titanium compound of about 10:1 to 3:1.

7. The process of claim 6 wherein said titanium compound is $(C_5H_5)_2TiCl_2$, the solubilizing agent is napthalene, the temperature is about 25° C. and the initial molar ratio of lithium metal to titanium compound is about 4:1.

* * * * *